United States Patent [19]

Thornton

[11] Patent Number: 4,830,021

[45] Date of Patent: May 16, 1989

[54] MONITORING SYSTEM FOR LOCOMOTOR ACTIVITY

[76] Inventor: William E. Thornton, 701 Cowards Creek Rd., Friendswood, Tex. 77546

[21] Appl. No.: 237,183

[22] Filed: Aug. 29, 1988

[51] Int. Cl.[4] .............................................. A61B 5/04
[52] U.S. Cl. .................................... 128/707; 128/779; 128/782
[58] Field of Search .............. 128/707, 709, 700, 670, 128/696, 774, 775, 776, 777, 778, 779, 780, 781, 782; 73/172; 272/69, DIG. 6; 340/573, 579

[56] References Cited

U.S. PATENT DOCUMENTS

| | | | |
|---|---|---|---|
| 3,717,857 | 2/1973 | Evans | 128/782 |
| 4,195,643 | 4/1980 | Pratt, Jr. | 128/779 |
| 4,211,238 | 7/1980 | Shu et al. | 128/700 |

Primary Examiner—Max Hindenburg
Assistant Examiner—Scott Getzow
Attorney, Agent, or Firm—Keith D. Beecher

[57] ABSTRACT

A system for monitoring human locomotor activities over long periods of time by recording acceleration ($G_z$) of the subject during such time periods, and by then converting acceleration to foot/ground forces ($F_z$) of the particular subject by a previously calibrated conversion table relating to that particular subject.

13 Claims, 7 Drawing Sheets

DATA ANALYZIER UNIT-400

MONITORING SYSTEM FOR LOCOMOTOR ACTIVITY

BACKGROUND OF THE INVENTION

Human locomotor activities such as walking, jogging and running, involves the largest muscles and bones in the body, and must be supported by the cardiovascular, respiratory, metabolic and nervous systems. This activity normally determines the capacity or condition, not only of the leg and backbones and muscles, but also of the heart, lungs and influences the amount of fat in the body and bloodstream. Knowledge of human locomotor activity is essential to both research and clinical practice in such diverse areas as physical conditioning, weight control, prevention of osteoporosis, cardio respiratory conditions, and the maintenance of condition of individuals in space flight.

The acquisition of knowledge of human locomotor activity has been hampered by the lack of a practical means for the continuous measurement of the key locomotor parameters. These parameters include the vertical foot/ground forces ($F_z$) generated in each step of the individual, as well as the number and rate of the steps over a prolonged period of, for example, 24 hours, or longer; as well as the lack of a practical means for determining the posture of the subject (lying, sitting or standing) during such activity. Also, the lack of practical means for determining the simultaneous effect of the activity on certain body systems, for example, heart rate, has also hampered the acquisition of the aforesaid knowledge.

In order to monitor human locomotor activity, it is essential that the vertical foot/ground forces ($F_z$) of the subject be measured over prolonged periods of time. Isolated measurements of the foot/ground forces of the subject have been made in the prior art by means, for example, of a "force plate", which comprises a platform with force recording elements between it and the ground. More recently, special shoes have been instrumented to measure the vertical foot/ground forces over a number of steps. However, such instrumented shoes are complex, custom made, difficult to use, and they have a high failure rate. Even if the problems of measuring the foot/ground forces over prolonged periods of time were solved, there still would remain in the prior art the problem of the practical recording, reproduction and manipulation of data over the prolonged period representing tens of thousands of cycles per day.

The present invention provides a practical means for solving the foregoing problems. Basically, the system of the invention continuously records the vertical acceleration (Gz) of the subject's center of gravity over the prolonged period. This represents a simple procedure as compared with any effort to record directly the vertical foot/ground forces ($F_z$) over such prolonged periods. The system then relates the characteristic acceleration signals of the locomotor steps of the subject with the foot/ground forces ($F_z$) associated with the individual's acceleration signature.

Accordingly, the system of the invention is capable of providing vertical foot/ground force data over prolonged periods of activity of the subject. Such foot/ground force data, as noted above, are essential in analyzing the effects of human locomotor activity on the muscles and bones of the body. In addition, the system of the invention provides data relating to other parameters of interest, such as the posture (lying, sitting or standing) and heart rate of the subject, as well as real time. A feature of the system of the invention is the provision of rapid means for processing and manipulating the data.

The embodiment to be described is concerned with vertical foot/ground force data because in most cases horizontal foot/ground forces are insignificant and may be neglected. However, it will become apparent as the description proceeds that the same techniques may be used to measure horizontal foot/ground forces, if so desired.

DETAILED DESCRIPTION OF THE ILLUSTRATED EMBODIMENT

Figure 1:
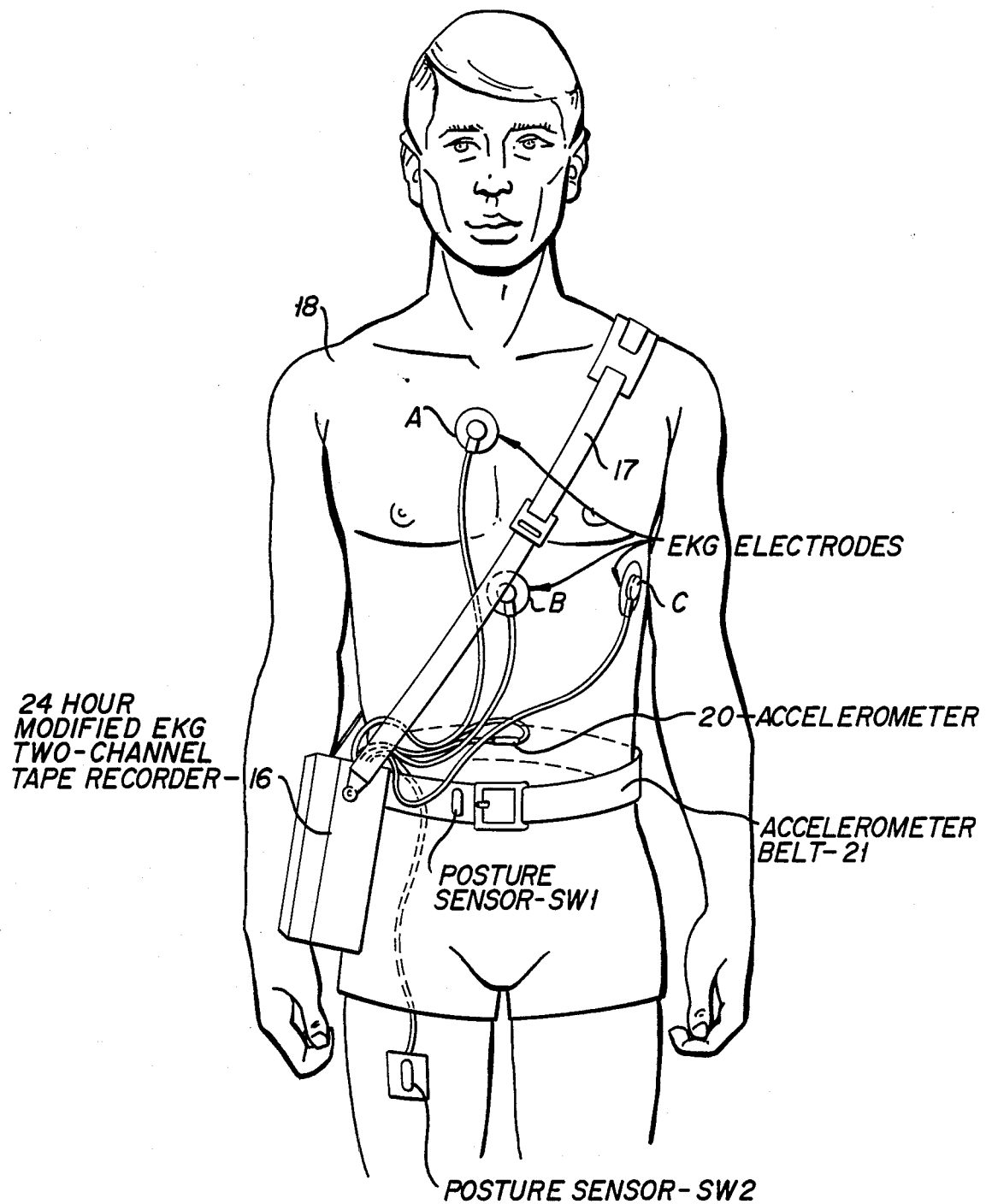
FIG. 1 is a representation of a subject on which various sensors and other instruments are mounted for carrying out the desired monitoring functions.

In order for the system of the invention to carry out its human locomotor monitoring function, it is necessary for the subject (shown as 18 in FIG. 1) to carry certain equipment. For example, the subject 18 carries a modified two-channel miniature EKG tape recording 16 on a shoulder strap 17. The subject also carries a miniature accelerometer 20 on a belt 21, the accelerometer measuring vertical accelerations ($G_z$) of the subject at his center of gravity. EKG electrodes A, B and C are also attached to subject 18 at predetermined positions on the subject. These electrodes are connected to recorder 16 by appropriate electric lead. Two position sensor switches SW1, SW2 are also attached to the subject, one on his waist and the other on his thigh. Switches SW1 and SW2 may be commercially available mercury gravity switches, or any other appropriate gravity switches may be used.

Figure 2:
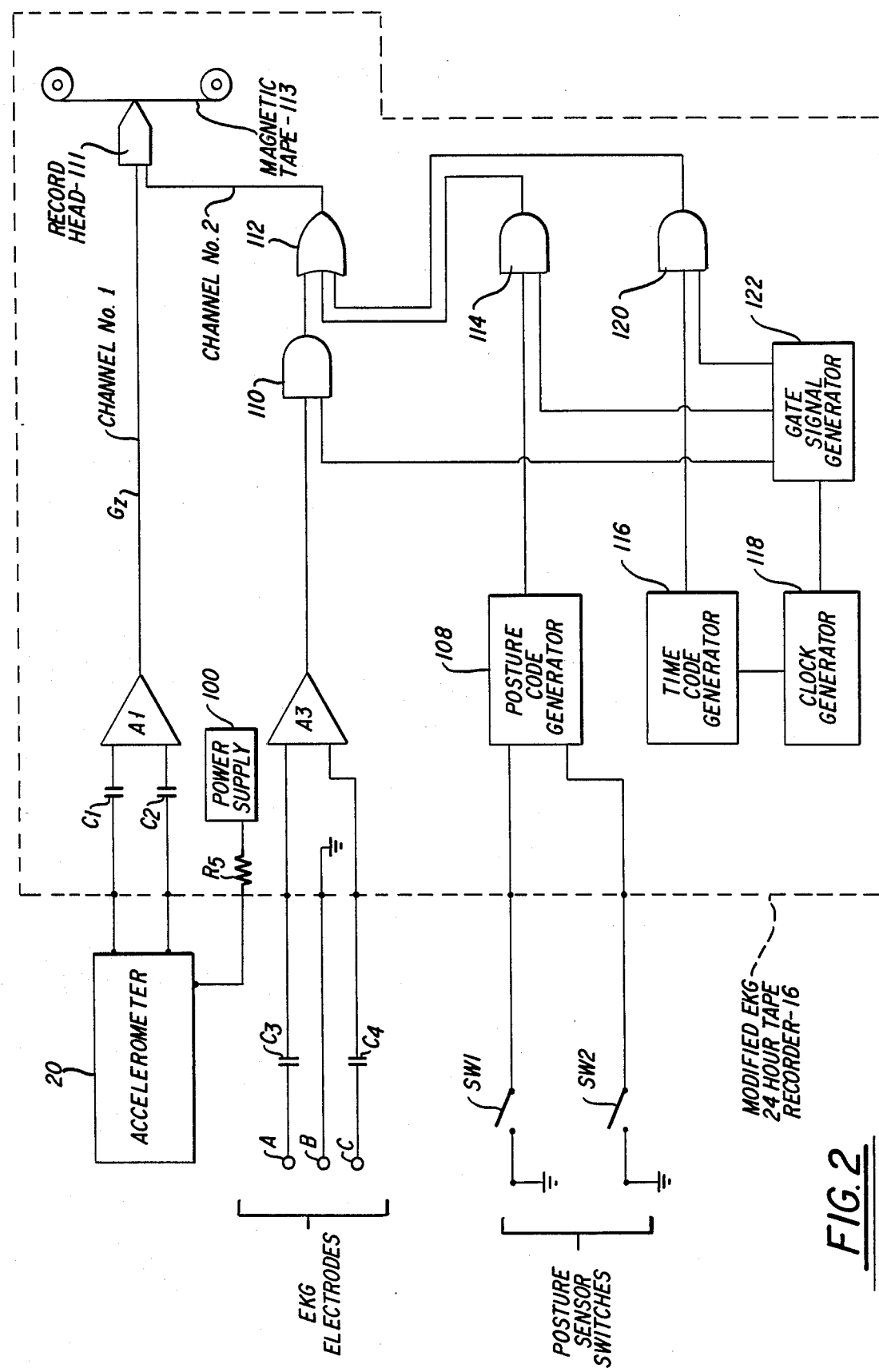
FIG. 2 is a schematic diagram of circuitry included in a recorder mounted on the subject for recording data pertaining to the subject.

The electronic circuitry associated with recorder 16 and the various sensors carried by subject 18 is shown in FIG. 2. In the embodiment under consideration, EKG data is used in the monitoring function and, for that reason, and since a proven 24 hour commercial EKG recorder, including playback, exists in the prior art, it was expedient for recorder 16 to take the form of a modified two-channel existing EKG recorder. Accordingly, the acceleration signal derived from accelerometer 20 ($G_z$) is recorded in channel #1 on magnetic tape 113 of the recorder by record head 111; and the EKG and posture signals, together with appropriate time signals, are recorded on channel #2.

Figure 3:
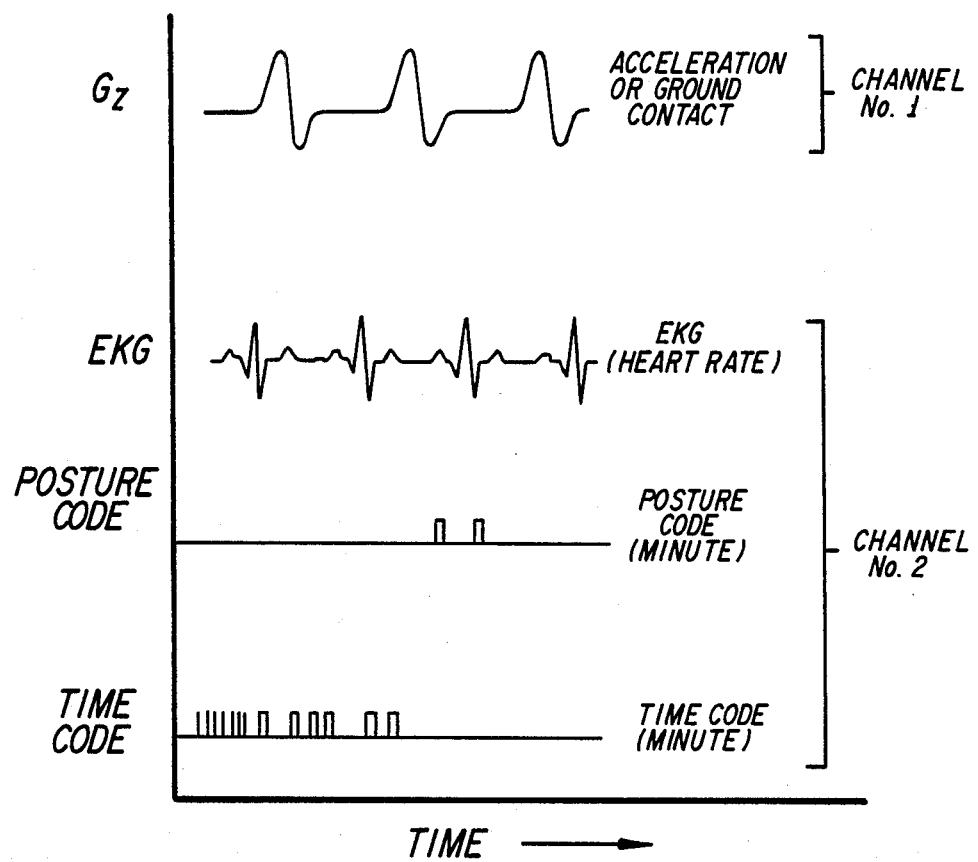
FIG. 3 is a series of curves representing data recorded on the recorder of FIG. 2.

With reference now to FIG. 2, accelerometer 20 may take the form of any conventional solid state accelerometer sensitive in one axis, and which is used to generate signals representing the vertical acceleration ($G_z$) of subject 18 at his center of gravity. The accelerometer is connected to channel #1 of the recorder 16 through capacitors C1 and C2 and amplifier A1. Power for the accelerometer 20 may be derived from the power supply 100 of the recorder through an appropriate scaling resistor R5. The resulting vertical acceleration ($G_z$) is recorded on channel #1 of the recorder 16 as shown by the curve $G_z$ of FIG. 3.

The EKG signals from electrodes A, B and C are passed through capacitor C3 and C4 and they are amplified by amplifier A3. The resulting amplified EKG signals are passed through an "and" gate 110 and through an "or" gate 112 to the record head 111 to be recorded on channel #2 on the magnetic tape 113.

The posture sensor signals from switches SW1 and SW2 are introduced to a posture code generator 108 in the modified recorder 16. Switches SW1 and SW2 are controlled, such that when the subject 18 is standing, both switches are closed; when the subject is sitting, switch SW2 is open and SW1 is closed; and when the subject is lying down, both switches SW1 and SW2 are open. Accordingly, the posture code generator 108 generates a digital code signal representing the posture of the individual during any phase of the activity. However, analog, frequency shift, or other types of coding may be used. This latter signal is passed through an "and" gate 114 to "or" gate 112, and is represented by the curve designated "Posture Code" in FIG. 3.

The modified recorder 16 also includes a time code generator 116 which is controlled by a clock generator 118, and which develops time code signals which are introduced to an "and" gate 120. These signals are shown on the curve designated "Time Code" in FIG. 3. Signals from the "and" gate 120 are passed through "or" gate 112 to the record head 111 likewise to be recorded on the second channel. However, the time code is used not only with respect to the EKG signals, but also with respect to the acceleration signal $G_z$ recorded on channel #1. The "and" gates 110, 114 and 120 are controlled by a gate signal generator 122 which also is timed by the clock generator 118.

As will be described, during the monitoring operation, the total time of the monitoring is divided into equal spaced time intervals of, for example, 1 minute, and the vertical acceleration signals ($G_z$) are analyzed over that particular interval. During each interval, the gate signal generator 122, at a particular time, closes gate 110 to terminate the EKG signal, and first opens gate 120 to enable the time code representing the particular interval to be recorded on channel 2 of the tape, and then closes gate 120 and opens gate 114 to enable the posture code representing the posture of the subject to be recorded, likewise for a brief interval. Then, the system reverts to its previous condition in which both gates 114 and 120 are closed and gate 110 is open, so that the EKG of the subject may be recorded in channel #2.

The result is a continuous recording of the $G_z$ vertical acceleration signal on channel #1 during the monitoring time; together with a recording of the EKG. However, the EKG is interrupted during each predetermined time interval to interpose the time code and the posture code for the corresponding time interval.

The system of the invention is calibrated to each individual, as mentioned above, by storing in a computer, or the like, a reference table which automatically relates the vertical acceleration signals ($G_z$) of the subject's center of gravity to the corresponding foot/ground force vertical signals ($F_Z$). By this conversion, the ($F_Z$) signals for each individual over prolonged periods of time may be obtained.

Figure 4:
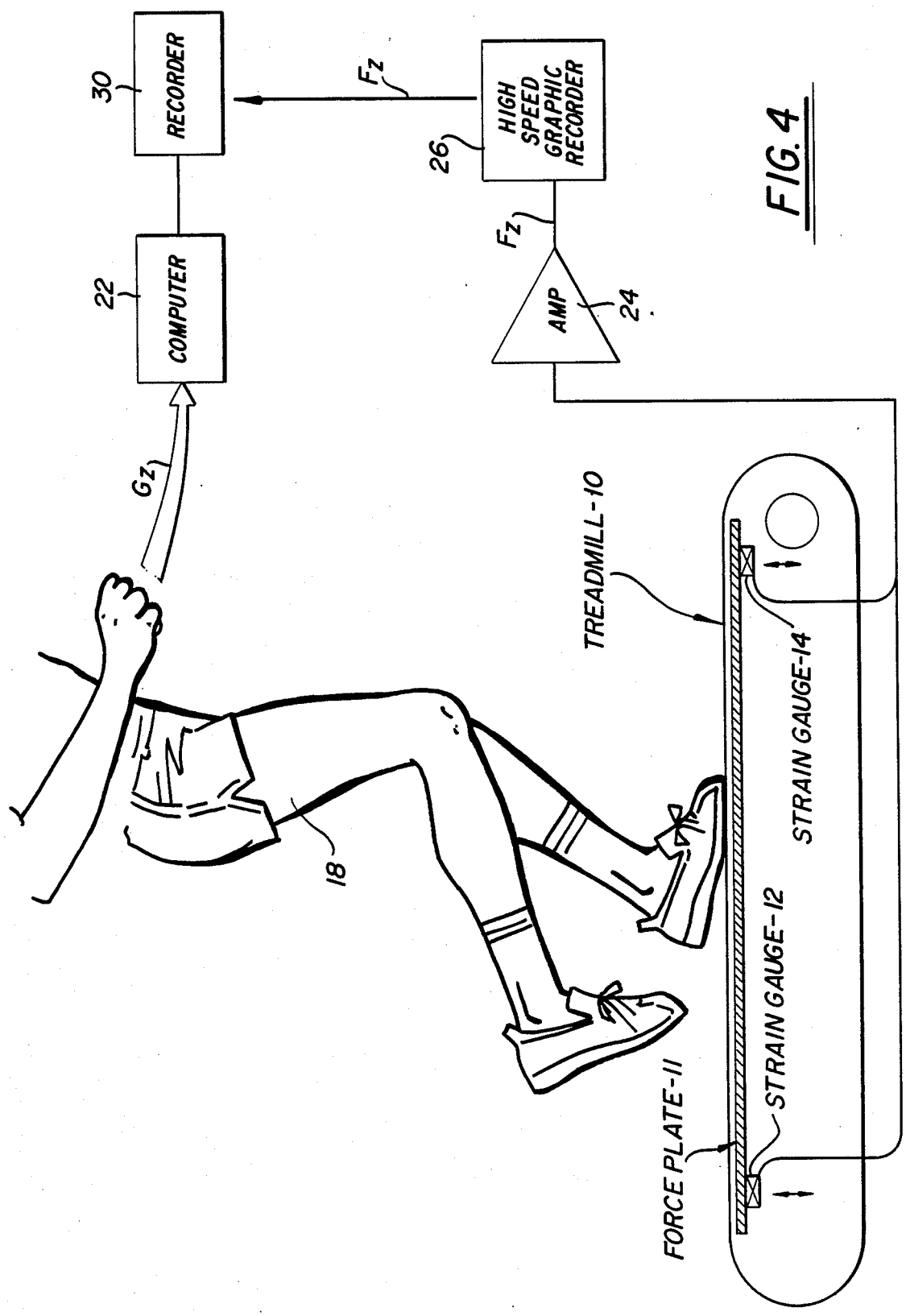
FIG. 4 is a representation of the subject positioned on a treadmill modified in accordance with the concepts of the invention to record the vertical ground forces of the subject.

Accordingly, the system is calibrated for each individual by having the subject 18 walk, jog and run on a treadmill 10 shown in FIG. 4. Treadmill 10 is equipped with a force plate 11 which is sensitive to forces in the vertical direction only. A vertical foot/ground force signal ($F_Z$) is sensed by strain gages 12 and 14 for each step of the subject on the treadmill. This foot/ground force signal ($F_Z$) is amplified by amplifier 24, and may be introduced to a high speed graphic recorder 26.

While the individuals is on the treadmill, he carries the equipment described above in conjunction with FIGS. 1 and 2, so that his vertical acceleration signals $G_z$, appropriately time coded, may be simultaneously recorded. Subsequently, the recorded $G_z$ signals are played back into a computer 22, as are the vertical foot/ground force signals ($F_Z$) recorded in the high speed graphic recorder 26. These two signals are precisely synchronized as to time, so that for any instant, the $F_Z$ signal represents the ground force signal corresponding to the vertical acceleration signal $G_z$ at that particular instant. Computer 22 then computes the mean $G_z$ signal over each successive predetermined interval, and the mean $F_Z$ signal over the same interval, and stores a conversion curve, such as shown in FIG. 5 in its memory.

Figure 5:
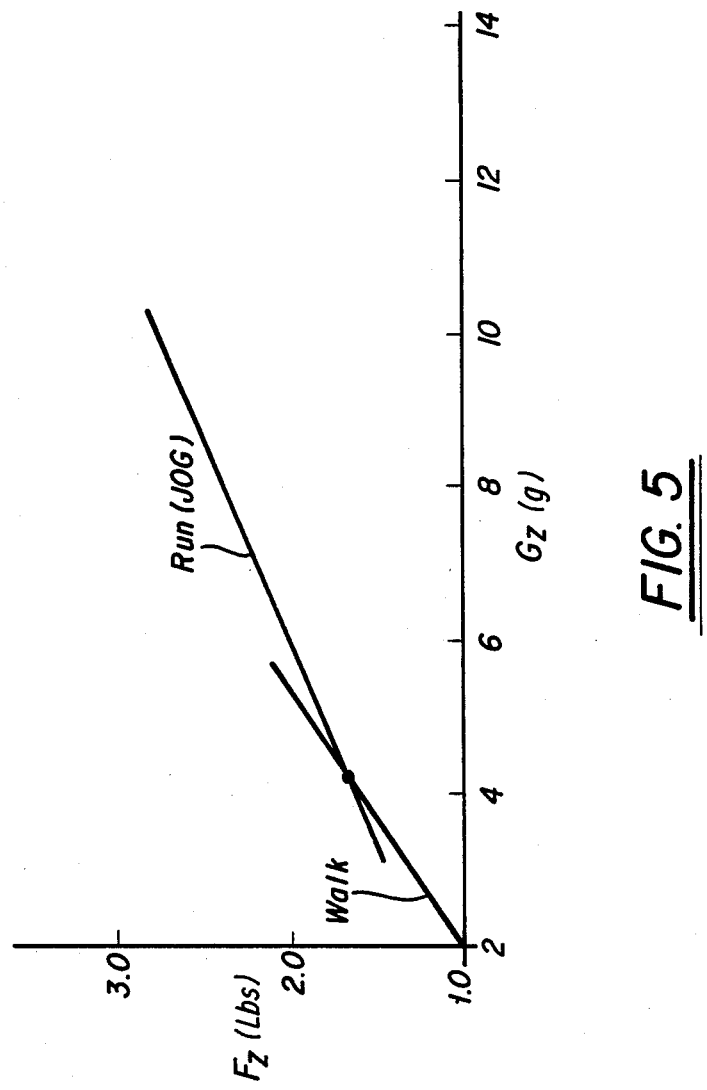
FIG. 5 is a curve representing a conversion table which is stored in the system of the invention and which is used for converting acceleration signals derived from the subject with corresponding vertical force signals related to that particular subject.

During the calibration procedure, while the subject is on the treadmill, as shown in FIG. 4, the subject first walks for a predetermined time, and as the speed of the treadmill is increased, the relationship between ($F_Z$) and ($G_z$) increases in an essentially linear relationship as shown by the line designated "Walk" in FIG. 5. At a particular point, as the speed of the treadmill 10 is further increased, the subject 18 jogs and/or runs, and the relationship between ($F_Z$) and $G_z$ then extends in a linear manner along a second line designated (jog) run which is inclined to the walk line as shown.

The curve of FIG. 5 represents a signature curve for the particular individual so that for that individual, whenever $G_z$ measurements are made, those measurements may be converted to the corresponding vertical foot/ground forces ($F_Z$) generated by that individual.

Treadmill 10 with its vertical force indicating capacity is described in more detail in Copending Application Ser. No. 237,069 filed Aug. 29, 1988 in the name of the present inventor. Instrumentation for the treadmill consists of mounting the usual treadmill belt support plate 11 on strain gages 12 and 14 or other force measuring instruments. Multiple gages must be used and balanced so that the forces registered are equal. In practice, there are balanced commercial strain gages available which may be connected in parallel and to a single amplifier, such as amplifier 24, or multiple amplifiers may be used and balanced. It is preferred to mount four strain gages, such as strain gages 12 and 14, under the force plate in FIG. 1 at the four corners of the force plate. This allows the vertical forces transmitted to the force plate to be accurately registered by the gages. The four gates may be connected in parallel.

To sum up, therefore, the first step in the operation of the system of the invention is to obtain data from the subject while on a treadmill, so that an appropriate transfer curve relating the vertical acceleration at the center of gravity of the individual to his vertical ground force signals may be obtained. After the calibration has been made, the individual is then free to pursue his normal activities for one or more days while wearing the equipment. During this interval, his time coded acceleration signals ($G_z$) are recorded by recorder 16, and his EKG signals and posture signals are also recorded.

Subsequently, the tape is played back at high speed into a computer which stores the transfer curve, so that the acceleration signals ($G_z$) may be transformed into the equivalent vertical foot/ground force signals ($F_Z$). Techniques are well known for recording physiological signals in the range of 0.05-100 Hz at slow magnetic tape speeds, or more recently by digital storage, to allow recording for 24 hours in recorder 16 on miniature reels or cassettes. The cassettes are subsequently replayed at 60-480 times the recording speed for rapid analysis. The system is well suited for recording the acceleration signals ($G_z$) since it requires only about 0.5-30 Hz response.

The particular system under consideration requires a knowledge of the vertical peak force, the step rate of the individual, and the number of steps during the predetermined time intervals, as well as the summation of the peak forces, the posture of the individual, the EKG and heart rate. All of such data is stored in the system, which also includes appropriate means for displaying the data. From the vertical force signals, the parameters such as step rate, peak force, summed forces/time, and the like, may be derived and displayed. After calibration, this data is obtained over several weeks of normal activity, for example.

As mentioned above, in addition to the basic locomotion vertical force signals, there are frequently other associated parameters of interest which enhance the value of the basic force cycle record, such as posture and EKG. It should be noted, however, that the system is not limited to such additional parameters, but may monitor virtually any environmental condition such as heat, light, temperature or internal condition of the subject, such as respiration, blood pressure and the like.

Since data may be required for prolonged time intervals from the system of the invention, automatic means of analysis is essential. As mentioned above, typical parameters to be considered include: step rate, mean peak force per step to the subject, rate of change of the vertical forces, summed forces, summed peak forces, mean and instantaneous velocity, and so on.

The step rate, or step period, of the individual may be derived from the vertical foot/ground force signal ($F_Z$) by known circuitry, or by a commercially available electronic tachometer, the output of which is stored or displayed. Peak forces may be detected by a conventional peak detector circuit and, after passage through a filter circuit with a time constant suitable for the time interval being recorded or displayed. Rate of change of force and summed forces can easily be derived from the vertical foot/ground force signal ($F_Z$) by standard differentiators or integrators; while summed peak forces may be derived by digital addition over the desired time interval.

The final phase of making the system of the invention practical is the provision of appropriate automatic means for the high speed reduction of the data recorded in the recorder 16, as the magnetic tape from the recorder is played back into an appropriate data reduction unit. There are a number of high speed replay units available for EKG reduction and analysis, and such a unit may be modified for the reduction and analysis of data obtained in the present system.

Figure 6:
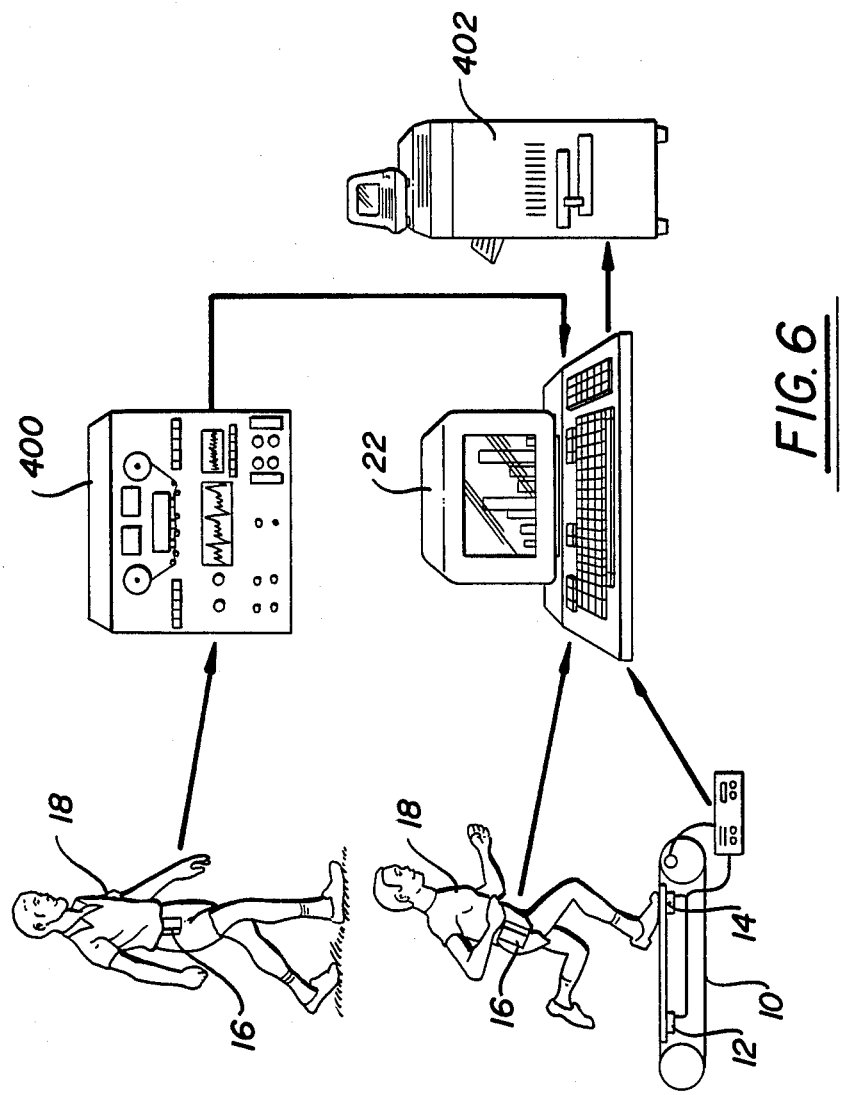
FIG. 6 is a diagram of the overall system of the invention in one of its embodiments.

An overall block diagram of the system in one of its embodiments is shown in FIG. 6.

As described above, the vertical acceleration data from the recorder 16 on the subject 18 while the subject is on treadmill 10 is played back to the computer and storage unit 22. At the same time, vertical force data ($F_Z$) from the treadmill is introduced to unit 22. The data is stored in unit 22 and a $F_Z/G_z$ conversion table for the particular subject is also stored, for example, on an appropriate memory disk.

Subsequently, the tape from recorder 16 bearing the data from subject 18 obtained over prolonged periods of time is replayed at high speed in a high speed data reduction unit 400 shown in FIG. 6. This unit may take the form of a modified Holter analyzer used, for example, in EKG reduction and analysis. The ($G_z$) data from unit 400 is then introduced to unit 22 in which it is converted by the stored $F_Z/G_z$ conversion data into corresponding ($F_Z$) signals. The latter signals are introduced to a plotter/printer 402 so that appropriate copies may be obtained.

For example, the data reduction time in unit 400 may be of the order of 120 times real time, as mentioned above. The unit 400 produce, for example, information relating to heart beats, steps taken by the subject, mean vertical acceleration, posture of the subject, and a time signal, for each minute during the prolonged period under consideration.

The data from the unit 400 is fed to unit 22 which serves as a storage means, as well as a data conversion/computation means. Accordingly, unit 22 produces data related to the vertical force, step rate, heart rate, posture as well as a summation of vertical forces.

The data from the unit 22 is then passed to the plotter/printer 402 which is capable of providing print-outs relating, for example, to vertical force versus time, heart rate versus time, posture versus time, and other data relating to each particular subject 18.

Figure 7:
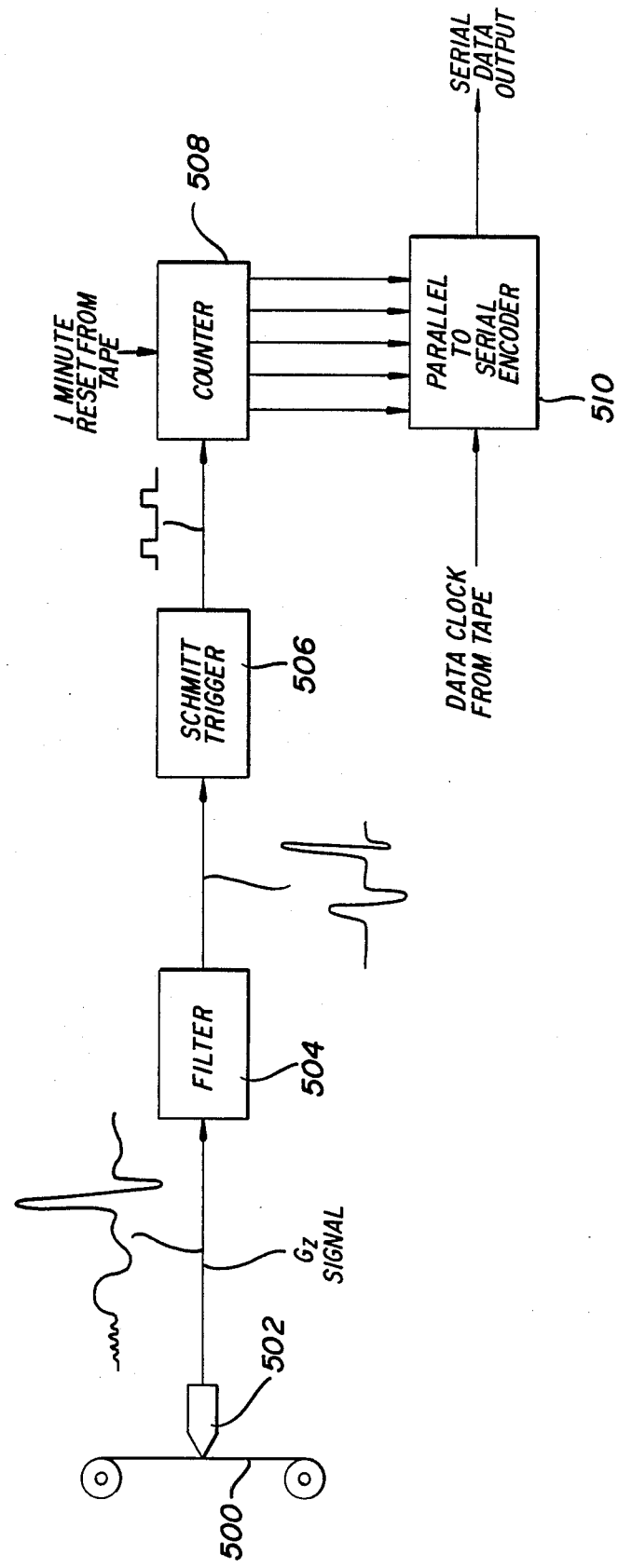
FIG. 7 is a block diagram showing certain components included in a data analyzing unit used in the system.

A general block diagram of the modified data analyzer unit 400 of FIG. 6 is shown in FIG. 7.

As mentioned above, the magnetic tape from recorder 16 bearing the acceleration ($G_z$) and other data is inserted into the analyzer unit, the tape being designated 500 in FIG. 7. The data on the tape is sensed by a reproduce head 502. As mentioned above, data is reduced, for example, during high speed replay of the tape at 120 times real time, and the data reproduced by the unit 400 is summed over 1 minute tape time intervals. In the unit, the acceleration signal ($G_z$) of each step of the individual 18 is detected. The acceleration signals ($G_z$) reproduced by head 502 are passed through a frequency responsive filter 504 which leaves only the fundamental components of the $G_z$ signal associated with each step. The signal is detected by a threshold device such as a Schmitt trigger 506 which, in turn, triggers counter 508. Counter 508 is reset after each 1 minute interval by a reset signal derived from the tape 500, and the output count of counter 508 represents a summation of the ($G_z$) signals over each 1 minute interval. The output from counter 508 is converted from parallel to serial form in an encoder 510. The encoder is clocked by a data clock from the tape so that the ($G_z$) data summed over each 1 minute interval may be fed to unit 22 in FIG. 6.

An important aspect of the system of the invention is the conversion of the acceleration data ($G_z$) from unit 400 into the corresponding vertical foot/ground force data ($F_Z$) for the particular individual 18 in unit 22. In the particular system, the summation ($G_z$) data over 1 minute intervals is digitized and stored in the unit 22 which, on program command and through well-known software techniques converts the ($G_z$) data to ($F_Z$) data through a conversion table stored in the computer which is individually generated and stored when the subject walks/runs on the instrumented treadmill while wearing the recorder/accelerometer, as described above. Other force characteristics such as rate of change of force may also be obtained in the same manner.

The data relating to the EKG and posture of the subject which are recorded on the second channel of tape 500 may also be processed over 1 minute intervals by conventional means. Once the overall data is replayed and stored in the system of the invention, it may be manipulated by software programming to provide digital and graphic information, as described above.

The system of the invention may be used in many ways and in many situations. For example, the clinician or researcher may be interested only in foot/ground forces ($F_Z$), and in such a case, a simple single channel time coded recording and replay system may be used. In space studies where both posture and ($F_Z$) vertical foot/ground force data are needed, a simple single channel scheme with multiplexed posture signals may be used. In other studies, the more complex system described above may be used.

Electronic technology is now such that the signal processing may be carried out in the recorder while data is being gathered. Accordingly, only values of certain parameters, such as step rate, acceleration, and the like, are stored digitally. This eliminates the necessity for tape replay, data conversion, etc. separately. It should also be noted that the recorder is not necessary should time and space be limited and processing may be carried out in real time.

If so desired, an estimated $F_Z/G_Z$ conversion curve may be stored in the computer for individuals of different age groups after many calibration curves have been obtained. Then close approximations may be made for individuals without the need to subject them to the calibration procedure.

The invention provides, therefore, an improved system for monitoring human locomotor activity over prolonged time intervals. The system uses the vertical acceleration $G_z$ of the subject, and compares that data with a previously stored conversion table, so as to derive the corresponding vertical ground forces associated with the particular subject.

It should be appreciated that while a particular embodiment of the invention has been shown and described, modifications may be made. It is intended in the claims to cover all modifications which come within the true spirit and scope of the invention.

I claim:

1. A system for monitoring human locomotor activity including: acceleration measuring means to be mounted on a subject for measuring accelerations of the subject; recorder means connected to the accelerometer means for recording data relating to such accelerations; a data analyzing unit coupled to said recorder and including storage means; sensor means responsive to locomotor activity of the subject for introducing reference ground force data into said data analyzing unit to be stored in said storage means, said data analyzing unit being responsive to the ongoing acceleration data recorded by said recorder for comparing said ongoing acceleration data with said reference ground force data stored in said storage means for converting the ongoing acceleration data into ongoing ground force data representative of the locomotor activity of the subject.

2. The system defined in claim 1, in which said acceleration measuring means measures vertical accelerations of the subject substantially at the center of gravity of the subject.

3. The system defined in claim 2, in which said ground forces stored in said data analyzing unit represent vertical ground forces.

4. The system defined in claim 1, in which said data analyzing unit includes means for analyzing said acceleration data over successive predetermined time intervals.

5. The system defined in claim 1, and which includes means for causing said acceleration data recorded by said recorder to be introduced into said data analyzing unit at a speed substantially higher than the speed at which it was recorded.

6. The system defined in claim 1, in which said sensor means comprises a treadmill including sensor means responsive to such locomotor activity to generate electric signals representing said ground force data.

7. The system defined in claim 1, in which said ground force data comprises vertical force signals.

8. The system defined in claim 1, and which includes sensor means to be mounted on the subject for generating EKG signals and connected to said recorder means to enable said recorder means to record said EKG signals.

9. The system defined in claim 1, and which includes sensor means to be mounted on the subject to sense the posture of the subject, and means connecting said last-named sensor means to the recorder means for enabling the recording means to record signals related to the posture of the subject.

10. In a system for monitoring human locomotor activity, the combination of: a data analyzing unit including storage means; means coupled to said unit for introducing signals to said unit representing acceleration data of a subject over a prolonged time period; and further means coupled to said unit for introducing signals to said unit representing foot/ground force data of the subject over a short time interval to be stored in said storage means for subsequent comparison with said acceleration data signals for converting ongoing acceleration data signals into foot/ground force signals representative of the locomotor activity of the subject.

11. The combination defined in claim 10, in which said acceleration signals relate to vertical accelerations of the subject; and said foot/ground force signals represent vertical ground forces of the subject.

12. The combination defined in claim 10, in which said data analyzing unit includes means for analyzing said acceleration data signals and said ground force signals over successive predetermined time intervals.

13. The combination defined in claim 10, in which said acceleration signals represent vertical accelerations of the center of gravity of the subject.

* * * * *